United States Patent
Rosenberger et al.

(10) Patent No.: US 8,589,179 B2
(45) Date of Patent: Nov. 19, 2013

(54) METHODS AND APPARATUS FOR RESPONDING TO REQUEST FOR CLINICAL INFORMATION

(75) Inventors: Bryan Rosenberger, Pennsburg, PA (US); Timothy Eggena, Hamilton, GA (US); Robert Nary, Voorhees, NJ (US); Robert Hale, Atlanta, GA (US); Patrick Cline, Southlake, TX (US); Robert Ellis, Doylestown, PA (US)

(73) Assignee: QSI Management, LLC, Irvine, CA (US)

( * ) Notice: Subject to any disclaimer, the term of this patent is extended or adjusted under 35 U.S.C. 154(b) by 413 days.

(21) Appl. No.: 12/519,245

(22) PCT Filed: Dec. 20, 2007

(86) PCT No.: PCT/US2007/026270
§ 371 (c)(1),
(2), (4) Date: Jul. 24, 2009

(87) PCT Pub. No.: WO2008/079386
PCT Pub. Date: Jul. 3, 2008

(65) Prior Publication Data
US 2010/0036679 A1   Feb. 11, 2010

Related U.S. Application Data

(60) Provisional application No. 60/871,064, filed on Dec. 20, 2006.

(51) Int. Cl.
*G06Q 50/00* (2012.01)

(52) U.S. Cl.
USPC .......................................................... 705/2

(58) Field of Classification Search
USPC .......................................................... 705/2, 3
See application file for complete search history.

(56) References Cited

U.S. PATENT DOCUMENTS

| 5,737,539 A | 4/1998 | Edelson et al. |
| 6,073,106 A | 6/2000 | Rozen et al. |
| 6,988,075 B1 * | 1/2006 | Hacker ............................. 705/3 |

(Continued)

OTHER PUBLICATIONS

International Journal of Medical Informatics 61 (2001) 241-246, Li et al. "Building a Generic Architecture for Medical Information Exchange Among Healthcare Providers".

(Continued)

*Primary Examiner* — Gerald J. O'Connor
*Assistant Examiner* — Edward Winston, III
(74) *Attorney, Agent, or Firm* — Fish & Associates, P.C.

(57) ABSTRACT

A hub-spoke patient information service in which a patient's data can be obtained from a network of independent data sources through a centralized service. The hub of the service stores patient identification information and the spokes store the patient's clinical data. In a preferred embodiment, the spokes are independent sources (e.g. each spoke is generally unrelated to other spokes) and include hospitals, doctor offices, clinics, insurance companies, or other entities that store or track clinical data. Preferably, the data sources use a first authentication to properly identify or authentic the service. Once access is granted, the spoke sources are queried for the patient's data. In response, each data source provides the type of patient data available from the source. The user is shown the types of data available without generally showing the actual data. The user can then select the specific patient data to retrieve from the spoke sources.

17 Claims, 5 Drawing Sheets

(56) References Cited

U.S. PATENT DOCUMENTS

| | | | |
|---|---|---|---|
| 2004/0249677 A1* | 12/2004 | Datta et al. | 705/3 |
| 2005/0027995 A1* | 2/2005 | Menschik et al. | 713/193 |
| 2005/0043964 A1 | 2/2005 | Thielscher et al. | |
| 2005/0101841 A9* | 5/2005 | Kaylor et al. | 600/300 |
| 2005/0246205 A1 | 11/2005 | Wang et al. | |
| 2006/0129434 A1 | 6/2006 | Smitherman et al. | |
| 2007/0016450 A1 | 1/2007 | Bhora et al. | |
| 2007/0055552 A1 | 3/2007 | St. Clair et al. | |
| 2007/0078856 A1 | 4/2007 | Dettinger et al. | |
| 2007/0192137 A1 | 8/2007 | Ombrellaro | |
| 2007/0214016 A1 | 9/2007 | Bennett et al. | |

OTHER PUBLICATIONS

Connection for Health, Markle Foundation, Feb. 2005, "Linking Health Care Information: Proposed Methods for Improving Care and Protecting Privacy".

* cited by examiner

METHODS AND APPARATUS FOR RESPONDING TO REQUEST FOR CLINICAL INFORMATION

CROSS REFERENCE TO RELATED APPLICATIONS

This application claims the benefit to Provisional Application No. 60/871,064 filed Dec. 20, 2006. This and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

FIELD OF THE INVENTION

The field of the invention is medical data storage and retrieval.

BACKGROUND

When an individual visits a hospital, clinic, or physician, numerous patient records related to the visit are created. Patient records traditionally have been maintained in paper form by the provider responsible for creating the records, but more recently patient records are migrating to various electronic forms. As a result, significant efforts have been placed on creating a national/regional network for access to patient records, regardless of the location of the records, or the specific healthcare provider creating the records.

Numerous problems exist in developing a national/regional network for access to patient records. One problem is that there are hundreds of thousands of medical service providers (hospitals, clinics, doctor's offices, etc. . . . ) that operate more or less autonomously. As a result there is considerable inconsistency with respect to the software and equipment used to capture and store the data, the fields of data captured, the formats used, archiving policies, and so forth. A second problem is that each provider wants ultimate control over its own data, but wants easy access to data generated by others. Still a third problem is that patients want to keep their records confidential.

Several different systems have been proposed. A fully centralized approach is known where the data records are stored in a central record repository. (See e.g., US 2006/0129434 to Smitherman, US 2007/0055552 to St. Clair, US 2007/0016450 to Bhora). However, this model requires broad agreement among healthcare providers that all data records will be managed by a central authority. Moreover, the scaling, reliability, and privacy issues associated with a central record repository are formidable.

A fully decentralized approach is also known, which allows a provider to access records distributed across multiple healthcare database management systems as though they were stored locally at the provider. Using this approach, electronic records regarding a given patient can be assembled on demand to provide a complete healthcare history of the individual. For example, Connecting For Health consortium (see http://www.connecting-forhealth.org/assets/reports/linking_report_2_2005.pdf), provides a central store that only maintains: (a) name, address, age, gender and other non-unique patient identification information; and (b) links to records in the local databases. (See also e.g., US 2005/0246205 to Wang). A drawback to using a decentralized approach is that users can receive incomplete patient records because of the diverse set of data sources, and the inability to extract relevant information from some of the sources. Moreover, many providers can be unwilling or unable to manage a local infrastructure.

US 2005/0027995 to Menschik teaches a decentralized network for mediating peer-to-peer transfer of patent medical data including a plurality of decentralized agents associated with a health care provider and connected to a central network. Unfortunately, Menschik requires all peers to authenticate all other peers, which results in an unwieldy, distributed mesh of trust. Such an approach lacks scalability because the number of authenticated relationships increases on the order of $N^2$ where N is the number of peers in the system. The system becomes impractical for N anywhere near as large as that required for a national medical network.

In between the centralized and decentralized approaches are hybrid approaches where some patient records can be centralized and others are stored in a decentralized network. (See e.g., US 2007/0214016 to Bennett). There are several new problems with these hybrid approaches. For example, problems can arise in deciding whether to store a particular record in a centralized or local data store. In addition, the relative importance of a particular electronic healthcare record can change with the occurrence of contemporaneous events, and therefore the record might not be placed properly in the right data store.

Currently, there is no solution that resolves all of the problems. Consequently, there is still a need for a system that combines demographic, clinical, and other practice-related data from multiple independent data sources, that can be conveniently mined and scaled easily as new data sources are added to the system.

SUMMARY OF THE INVENTION

The present invention provides apparatus, systems and methods in which a patient's data can be obtained from a network of independent data sources through a centralized service. The service preferably comprises a hub-spoke network of data sources. The hub of the service stores patient identification information and the spokes store the patient's clinical data. In a preferred embodiment, the spokes are independent sources (e.g. each spoke is generally unrelated to other spokes) and include hospitals, doctor offices, clinics, insurance companies, or other entities that store or track clinical data.

In one aspect, users can log on to the service to access the patient's data. The patient's identification information can be used identify a set of "spokes" data sources having the patient's data. Preferably, the data sources use a first authentication to properly identify or authentic the service. Once access is granted, the spoke sources are queried for the patient's data. In response, each data source provides the type of patient data available from the source. The user is shown the types of data available without generally showing the actual data. The user can then select the specific patient data to retrieve from the spoke sources. At least a subset of the patient's is retrieved from at least one of the spoke source using a second authentication.

Various objects, features, aspects and advantages of the inventive subject matter will become more apparent from the following detailed description of preferred embodiments, along with the accompanying drawings in which like numerals represent like components.

DETAILED DESCRIPTION

Figure 1:
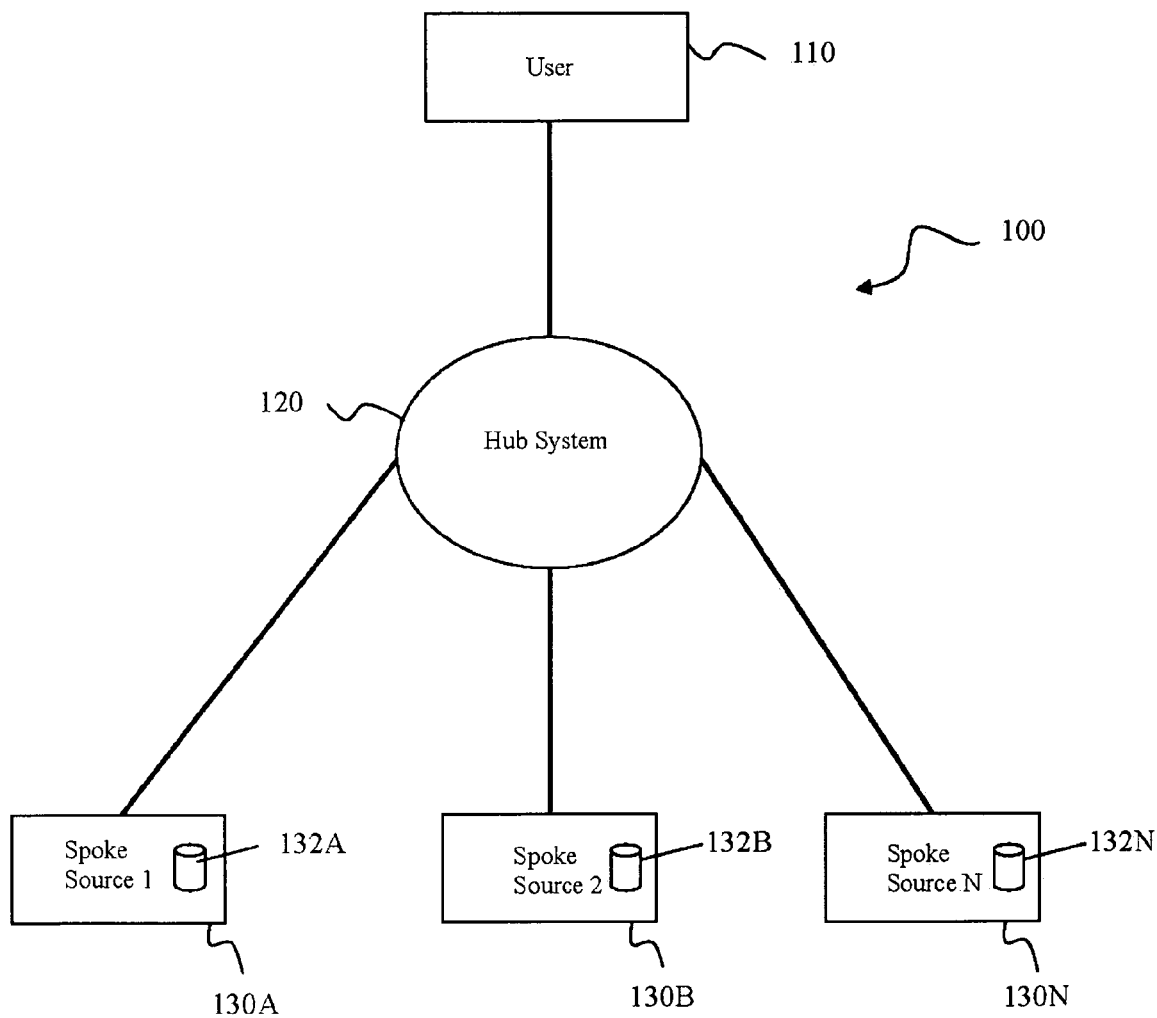
FIG. 1. is a schematic of a hub-spoke patient information service.

FIG. 1 is a block diagram illustrating the hub-spoke network 100 of the present invention. As shown, a user 110 can interact with the hub-spoke patient information service 120 to receive "patient clinical data" stored in the local data stores 132A, 132B, . . . 132N of spoke sources 130A, 130B, . . . 130N.

User 110 is defined as any doctor, hospital, clinic, healthcare organization, and/or research facility, geographically located anywhere that uses patient clinical data for the purposes of patient care and/or research regardless of where the data physically resides.

For purposes of the present invention, the "patient clinical data" of interest includes patient histories, medical records, lab tests, X-rays, prescriptions, diagnosis', treatment information, and other patient clinical data stored in a local "data store" 132A, 132B, . . . 132N at spoke sources 130A, 130B, . . . 130N. The term "data store" is used euphemistically to represent any storage of data including a file system, a web site, a database, or other system where data can be accessed.

Each of the spoke sources 130A, 130B, . . . 130N represent any individual, entity, or organization that provides health care related goods or services to, or on behalf of, a patient. For example spoke sources 100A, 100B, . . . 130N include primary care physicians, clinics, hospitals, research facilities, and other entities that provide healthcare services. Spoke sources 130A, 130B, . . . 130N can also include other healthcare related entities including pharmacies, pathology laboratories, insurance companies, rehabilitation centers, or other entities requiring access to the patients clinical data. More generally, spoke sources 130A, 130B, . . . 130N represent any entity that maintains a local data store of patient clinical data. For simplicity purposes only three spoke sources have been shown in FIG. 1, but it should be appreciated that spoke source 130N can represent an unlimited number of individuals, entities, or other organizations that maintain a local data store of patient clinical data. Further, the above-described hub-spoke network 100 can range in scope from being limited to a particular geographical region to being nationally or even internationally distributed.

It will be appreciated that privacy and security are important to the communication of patient clinical data. In the described embodiments, the various components of the hub-spoke network 100 communicate securely over the Internet using any suitable algorithms or protocols that provide confidentiality, authentication, or data integrity (e.g. HTTPS, SSL, SSH, AES, 3DES, PGP, RADIUS, Kerberos, or other security methods) or alternatively, hub-spoke network 100 can be configured to communicate over a virtual private network.

Figure 2:
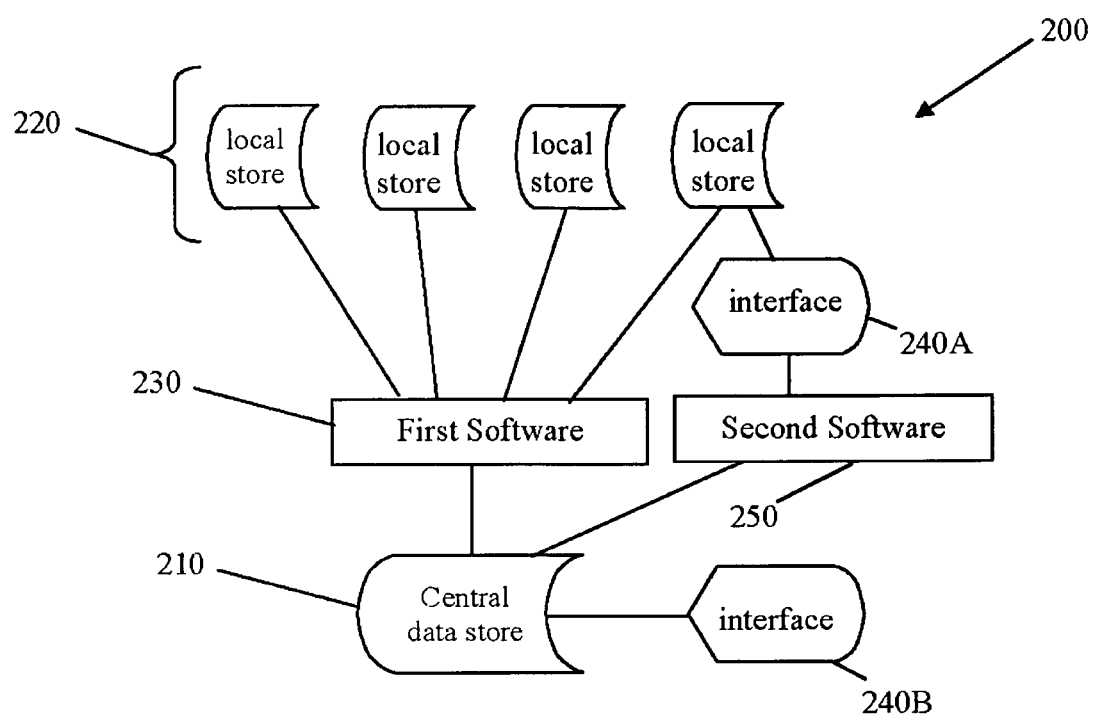
FIG. 2. is a schematic of a hub-spoke system having interfaces, a central data store, and a plurality of spoke source patient information systems that a first and second instance of software act upon.

FIG. 2 generally depicts a hub-spoke patient information service 200 including a central data store 210, and a plurality of spoke source data stores 220. The central data store 210, can include: (a) patient identification information and demographic information (FIG. 4, 410), (b) types of patient clinical data available from the spoke source data stores (FIG. 4, 420), (c) some but not all corresponding patient clinical data available (see FIG. 4, rows B, C) in the spoke source data stores 220; and (d) links (FIG. 4, as shown by the X's in the selection columns 450) to individual ones of the spoke source data stores 220 sufficient to access additional corresponding patient clinical data maintained in such spoke source data stores 220.

The systems and methods of the present invention can be implemented in any number of ways, preferably including at least one instance of a first software 230 that exports from spoke source data stores 220 to the central data store 210, and at least one instance of a second software 250 that uses the patient identification information to access additional corresponding patient clinical data in accordance with authentication controls, described below. Instances of both the first software 230 and the second software 250 can advantageously be implemented at the spoke source data stores 220, although one or both can also be implemented at the central data store 210, or elsewhere.

First software 230 extracts or at least transfers patient identification information and some types of patient clinical data available, generally without showing the patient's data falling within the types of but not all patient data to the central store 210. Of course, central data store 210 is logically, and not necessarily geographically central to the spoke source data stores 220, and indeed might itself be distributed or include some sort of edge cache. For example, first software 230 can be embodied by an SQL database storing store patient data. When the database is queried, the data can be collect and sent over a secure HTTPS link to a central service having the central data store.

Information stored in central data store 210 is accessible by any number of instances of interfaces (described below), two of which are shown here as interfaces 240A and 240B. Interface 240A could be operated, for example, by a physician or other personnel at a facility associated with one of the spoke source data stores 220. Interface 240A works with the instance of the second software 250 to pull information from the central data store 210 and possibly from one or more of the spoke source data stores 220 (according to authentication). Interface 240B could be operated, for example, by personnel at the Centers For Disease Control, or some other government or non-government agency, and would again pull information from the central data store 210 and possibly from one or more of the spoke source data stores 220 (according to authentication).

Figure 3:
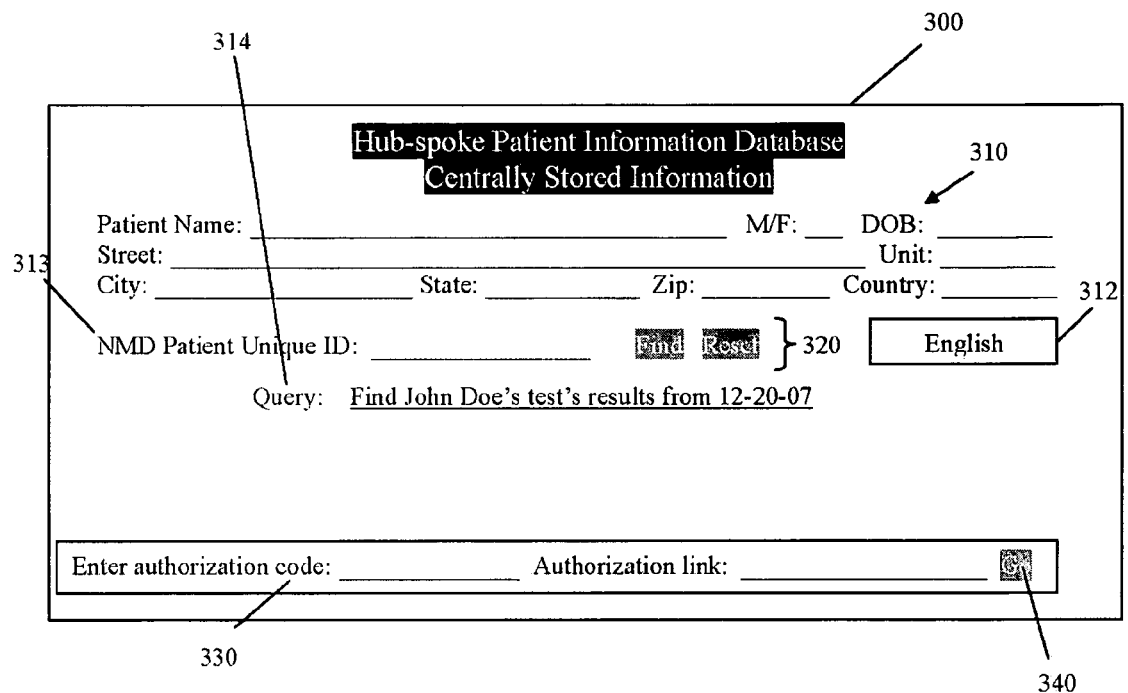
FIG. 3. is a schematic of an interface having patent identification information.

FIG. 3 generally depicts an interface 300 provides access to patient clinical data. In general, interface 300 includes a block for entering and displaying patient identification information and demographic information 310, and optionally a unique patient ID number 313. Action buttons 320 instruct the software to either find information relating to the patient or reset to blank out the display. Drop down language translation interface 312 allows users to interface in different languages. In still other aspects it is contemplated that a natural language interface 314 could be used for entering queries against the database. It yet additional aspects a statistical package (not shown) can be included to provide statistical output from queries against the database.

Figure 4:
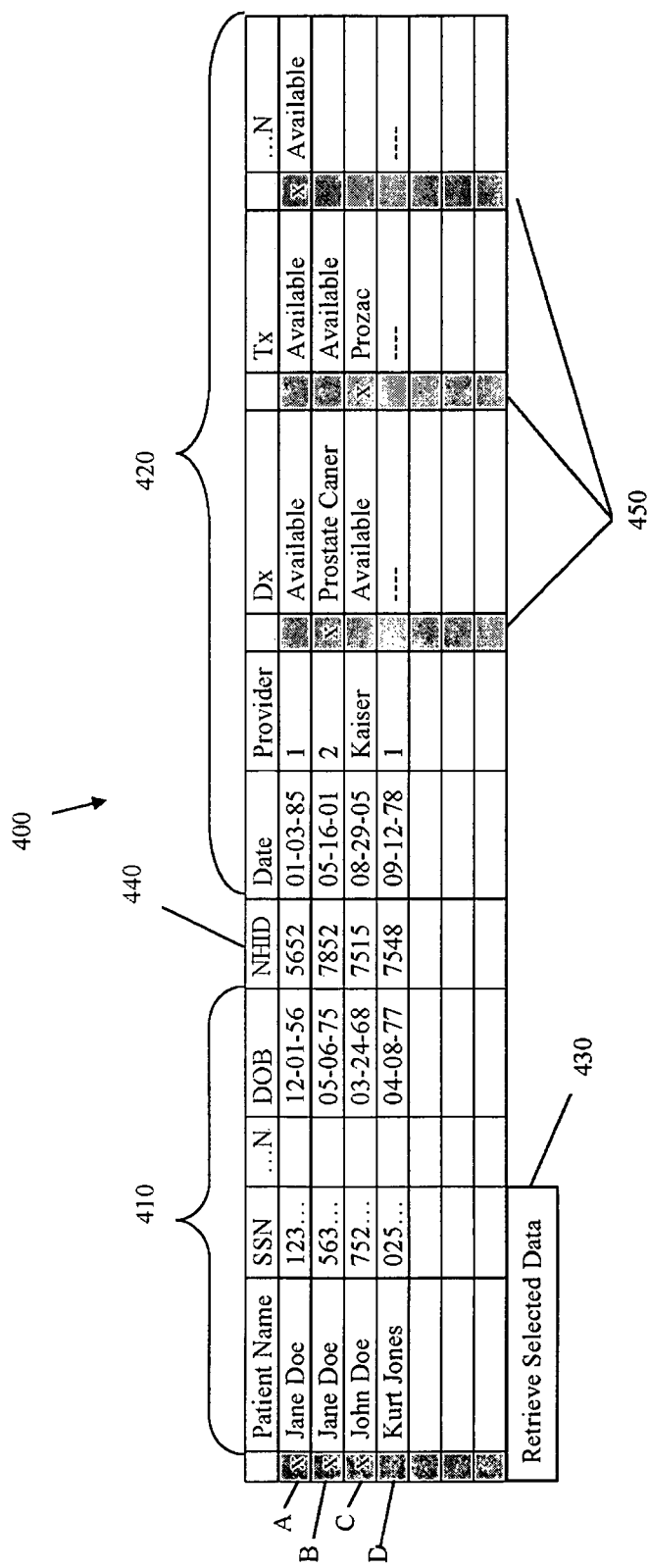
FIG. 4. is a schematic of a table showing types of patent data available from spoke sources.

FIG. 4 shows schematic of table 400 showing types of patent data available from spoke sources. The elements of FIG. 4 are provided to clarify the following description of FIG. 5, which depicts a schematic illustrating the steps of a method of obtaining a patient's clinical data using the hub-spoke system of the present invention.

In preferred embodiments, at step 510 the central data store stores some identification information of the patient (FIG. 3, 310). The central data store is generally located within a hub of a hub-spoke patient information system. The identification information of the patient can advantageously include a unique patient identifier (FIG. 3, 313) for all of the patients, as well as the patient's phone number, social security number, date of birth, address and other patient identification information and demographic information. On the other hand, it is contemplated that at least some of the medical providers will refuse to provide data linked to a unique patient identifier, and in those instances it is contemplated that a unique identifier will not be used. If enough medical providers refuse to provide data linked to a unique patient identifier, it is contemplated that the systems and methods described herein can operate without any unique patient identifiers.

At step 520, the hub-spoke patient information service authenticates a user that wishes to access the service. Additionally, a fee can be charged for accessing hub-spoke service, as shown by step 524. Preferred fees can include per usage fees, commissions, subscription fees, fees related to the quantity of data requested, or other compensation for usage of the hub-spoke service. Authentication of the user can be accomplished by a user name and password field using any suitable user authentication (e.g. RADIUS, Kerberos or other authentication methods). In preferred embodiments, step 520 includes step 522; providing a user with different levels of access depending on the user's access level.

For example, Level I access can be given to each individual patient, allowing a patient to: (a) at least partially control access by others to at least some of his/her own clinical data via the system; (b) at least partially determine a source of at least some of his/her own clinical data stored on the database; (c) at least partially determine information relating to historical queries against the database for at least some of his/her own clinical data stored on the database; (d) selectively release contact information for himself/herself to other non-medically related members of the public; (e) selectively release contact information for himself/herself to only certain classes of inquirers; and (f) sell information stored on the database for his/her own profit.

Level 2 access is given to the author of the medical records, for example the physician or other healthcare provider who created the record. An individual with Level 2 access can read all documents within the service as well as update and create new records. Level 3 access can provide access to an institution or group practice, wherein the patients will typically receive a variety of healthcare services that can come from any spectrum of inpatient, emergency, laboratory, imaging, and some other types of outpatient services associated with the institution or group practice. All healthcare providers who are registered as care providers under an institutional license are granted Level 3 access. Level 4 access can provide access under emergency circumstances, for example where a patient can be unconscious or otherwise non-responsive. Level 5 access can provide access to governmental agencies, for example the CIA, NSA, FBI, and other governmental agencies. One should appreciate that additional and/or different levels of access are contemplated.

Referring again to FIG. 3, after initial access is granted to the hub-spoke service at step 520, the user enters a patient's identification information and demographic information into interface 300, or alternatively a query into natural language query field 314; then the user clicks the find action button. Once the find action button is clicked, the hub-spoke patient information service at step 530 of FIG. 5 identifies a set of spoke sources having the patient's clinical data using a first authentication to authenticate the service with the set of spoke sources. The hub-spoke service uses the first authentication to simply find if a patient's clinical data is available at one of the spoke data stores. In preferred embodiments as shown by numeral 532 in FIG. 5, the first authentication can be common across the set of spoke sources. Any suitable method for system-to-system authentication can be used including using certificate authorities, authentications protocols (e.g. RADIUS, or Kerberos) or other security protocols. However, the first authentication is not required when the hub and spokes are trusted.

Figure 5:
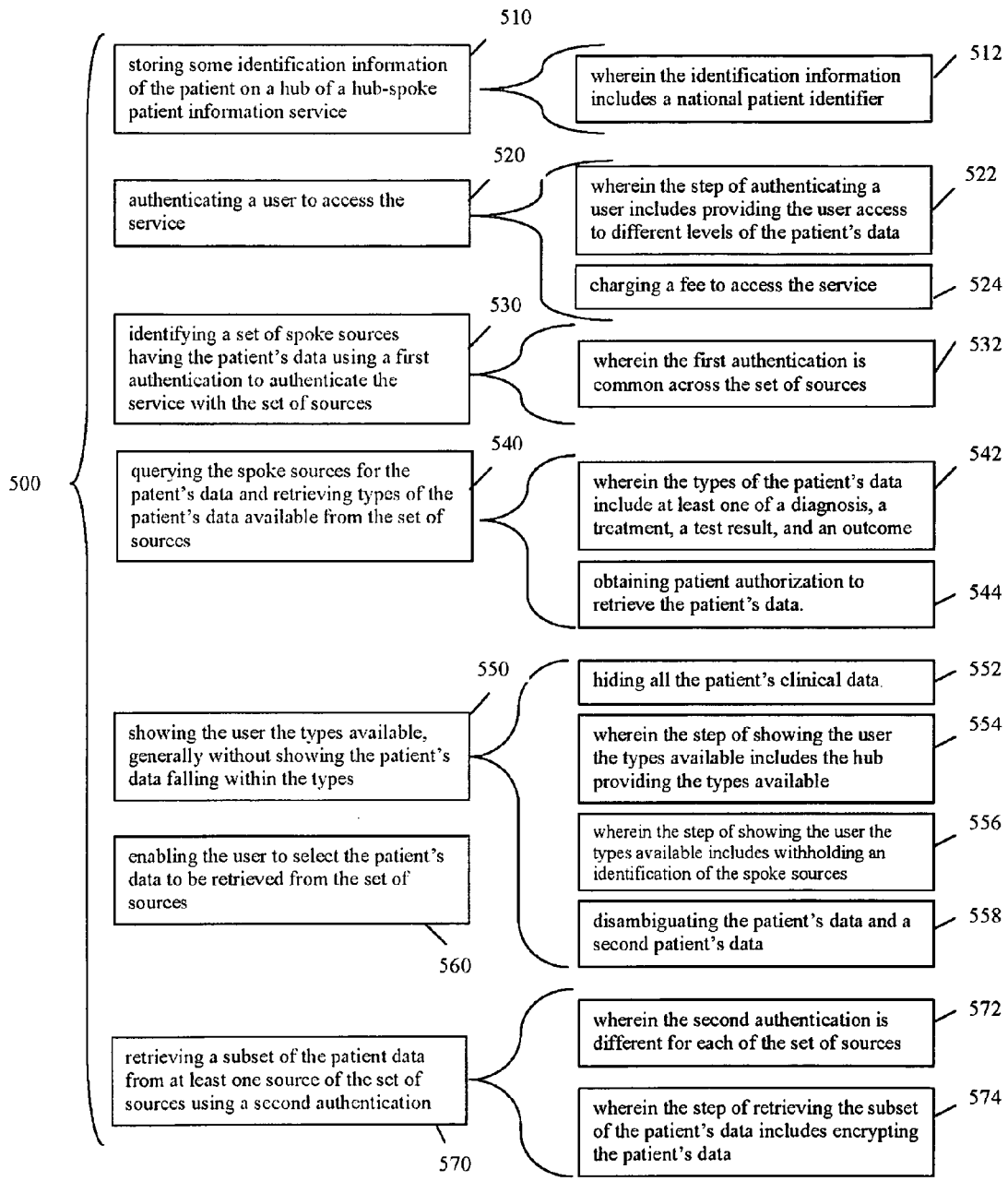
FIG. 5. is a schematic illustrating the steps of a method of obtaining a patient's clinical data using the Hub-Spoke network of the present invention

Upon authentication of the hub-spoke service with the identified spoke sources, at step 540 in FIG. 5, the hub-spoke service queries the spoke data stores for the patient's clinical data and retrieves types of the patient's data available (FIG. 4, 420) from the set of sources. The types of patient data available 420 can include the date the patient clinical data was made available (i.e. when it was created), diagnoses, treatment information related to the diagnosis, tests results, x-rays, outcomes, side effects related to the diagnosis, allergies, and other patient clinical data. For example, as shown in FIG. 4, the types of the patients clinical data available are Dx, Tx, . . . N. As contemplated, N represents any number of additional columns for displaying additional and/or different patient clinical data.

Optionally Step 540, can also include step 544, in which the hub-spoke service obtains a patient's authorization before retrieving a patient's clinical data. Preferred authorization methods include signed documents, electronic signature, or verbal authorization. In alternative embodiments, authorization information to retrieve information to table 400 in FIG. 4 can be provided by the user in block 330. Note that the authorization information can include a code, and/or possibly signature papers or other stored documents accessible by a link 340.

Once the patient clinical data is located on the central store, the hub-spoke service, at step 550, populates a table 400 (as shown in FIG. 4) with the retrieved information. Table 400 shows the user the types of patient clinical data available, as shown by numeral 420, "generally" without showing the actual patient's data falling within the types. For example, in row A of table 400, the system displays the types of data available (Dx, Tx, . . . N, as shown by 420) without showing any of the actual patient's clinical data. As referred to herein "generally" means that the hub-spoke service displays at least 75% of the types of data available 420, without showing the actual clinical data, as discussed above.

At step 558 in FIG. 5, the hub-spoke service disambiguates a first patient's data and a second patient's data. Disambiguation step 558, can preferably include the hub-spoke service employing probabilistic matching or simply showing additional data, including a unique patient ID (i.e. NHID 440), to distinguish multiple patient's data.

It is contemplated that step 550 can include the hub providing the types of data available, as shown by step 554 in FIG. 5, generally without showing the patient's data falling within the types. In an alternative embodiment, as shown by numeral 552 in FIG. 5, the hub-spoke service can hide all of the patient's clinical data, as shown by row D in FIG. 4, which can be the result of a user not having the proper level of access. In another embodiment, as shown by numeral 556 of FIG. 5, the hub-spoke service can withhold the identification of the spoke sources, as shown in rows A, B, and D in FIG. 4.

At step 560, the hub-spoke service enables the user to select the patient's clinical data to be retrieved from the set of identified spoke sources, as shown by the X's in selection columns 450 in FIG. 4. Thus, the user can readily seek to obtain additional information on any of the specific diagnoses, treatments, etc listed in table 400 by selecting the appropriate boxes in selection columns 450.

Once the user has selected the appropriate boxes for the patient's clinical information to be retrieved from the set of identified spoke sources, the user clicks on the retrieve selected data button 430. At step 570, the hub-spoke service retrieves a subset of the patient clinical data (i.e. selected data) from at least one of the set of spoke sources using a second authentication. In preferred embodiments, the retrieved information is displayed in a separate screen (not shown). Contemplated second authentication can include system-to-system authentication as describe previously. Additionally, it is contemplated that data exchange of confidential patient data can be performed using suitable encryption techniques or protocols (e.g. AES, 3DES, SSL, SSH, HTTPS, or other secure data exchanges).

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps can be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of obtaining patient's clinical data, the method comprising:
    storing identification information of a patient on a hub of a hub-spoke patient information service, wherein the hub is communicatively coupled with a set of spoke sources storing clinical data of the patient associated with a plurality of different types of clinical data;
    authenticating a user to access the hub;
    upon receiving a request by the user, querying the set of spoke sources using a first authentication to authenticate the hub with the set of spoke sources;
    retrieving, by the hub immediate after receiving the request, a first subset of clinical data of the patient available to the user from the set of spoke sources based on the first authentication;
    providing a user interface, by the hub, that presents to the user a clinical data report comprising the first subset of clinical data retrieved by the hub, wherein the clinical data report lists the plurality of different types of clinical data, generally showing the subset of patient's clinical data falling within some, but not all, of the types, wherein each type of clinical data is shown with an indicator indicating whether the type of clinical data is or is not available for the user to retrieve;
    enabling the user to select a type of clinical data to be retrieved from the set of spoke sources;
    retrieving, by the hub, a second subset of the clinical data from at least one spoke source of the set of spoke sources using a second different authentication; and
    providing a new user interface for the user by including the second subset of the clinical data in the clinical data report.

2. The method of claim 1, further comprising obtaining patient authorization to retrieve the patient's clinical data.

3. The method of claim 1, further comprising disambiguating the patient's first subset of clinical data and the second subset of clinical data.

4. The method of claim 1, wherein the plurality of different types of clinical data include at least one of a diagnosis, a treatment, a test result, and an outcome.

5. The method of claim 1, wherein the patient's identification information includes a national patient identifier.

6. The method of claim 1, further comprising hiding all the patient's clinical data.

7. The method of claim 1, further comprising showing the user a date corresponding to a time when the patient's clinical data became available.

8. The method of claim 1, wherein the clinical data report lists the plurality of different types of clinical data without showing an identification of the spoke sources.

9. The method of claim 1, wherein the step of authenticating a user includes providing the user access to different levels of the patient's clinical data.

10. The method of claim 9, further comprising enabling the patient to authorize access to the different levels of the patient's clinical data.

11. The method of claim 1, further comprising providing a natural language interface to query the service for the patient's clinical data.

12. The method of claim 1, further comprising providing a language translation interface to display the patient's clinical data in a selected language.

13. The method of claim 1, wherein the second authentication is different for each of the set of spoke sources.

14. The method of claim 1, wherein the step of showing the user the types available includes the hub providing the types available.

15. The method of claim 1, wherein the step of retrieving the subset of the patient's clinical data includes encrypting the patient's clinical data.

16. The method of claim 1, wherein the first authentication is common across the set of spoke sources.

17. The method of claim 1, further comprising charging a fee to access the service.

\* \* \* \* \*